United States Patent [19]

Ratner

[11] Patent Number: 5,357,951
[45] Date of Patent: Oct. 25, 1994

[54] CARDIAC PULMONARY RESUSCITATOR APPARATUS VALVE WITH INTEGRAL AIR SAMPLING PORT

[75] Inventor: Jeff B. Ratner, Pinellas Park, Fla.

[73] Assignee: Mercury Enterprises, Inc, Clearwater, Fla.

[21] Appl. No.: 71,071

[22] Filed: Jun. 2, 1993

[51] Int. Cl.⁵ ............................ A62B 9/02; A62B 7/10; A62B 23/02
[52] U.S. Cl. ........................ 128/205.24; 128/205.13; 128/205.29; 128/205.12; 128/909; 128/912
[58] Field of Search ....................... 128/202.28, 202.29, 128/203.11, 204.22, 205.13, 205.23–205.25, 205.29, 205.12, 909, 912

[56] References Cited

U.S. PATENT DOCUMENTS

| | | | |
|---|---|---|---|
| 3,196,866 | 7/1965 | Adams | 128/205.13 |
| 4,811,730 | 3/1989 | Milano | 128/203.11 |
| 4,945,918 | 8/1990 | Abernathy | 128/202.22 |
| 5,109,840 | 5/1992 | Daleiden | 128/205.23 |
| 5,163,424 | 11/1992 | Kohnke | 128/205.13 |
| 5,213,096 | 5/1993 | Kihlberg et al. | 128/912 |

FOREIGN PATENT DOCUMENTS

| | | | |
|---|---|---|---|
| 0139363 | 5/1985 | European Pat. Off. | 128/205.13 |
| 910065 | 11/1962 | United Kingdom | 128/205.13 |
| 2139099 | 11/1984 | United Kingdom | 128/205.13 |

OTHER PUBLICATIONS

"The Mercury CPR Bag" catalog produced by Mercury Enterprises, Inc. date unknown existed at least Jan. 31, 1990.

"Laerdal Silicone Resuscitaters" catalog produced by Laerdal Medical Corp. Date unknown. Existed at least Jan. 31, 1990.

*Primary Examiner*—Kimberly L. Asher
*Attorney, Agent, or Firm*—James E. Larson; Herbert W. Larson

[57] ABSTRACT

The cardiac pulmonary resuscitator improved patient valve has a top and bottom portion joined together forming a cylindrical housing. A diaphragm is mounted between the housing top and bottom portions through which air passes to and from the patient. A rigid tubular port integral with the top portion has a first opening outside the housing and a second opening inside the top portion. A pair of stops on each side of the second opening prevents the diaphragm from blocking air into the rigid tubular port so that some air to and from the patient flows through the rigid tubular port to an air sampling device for making a reading.

16 Claims, 4 Drawing Sheets

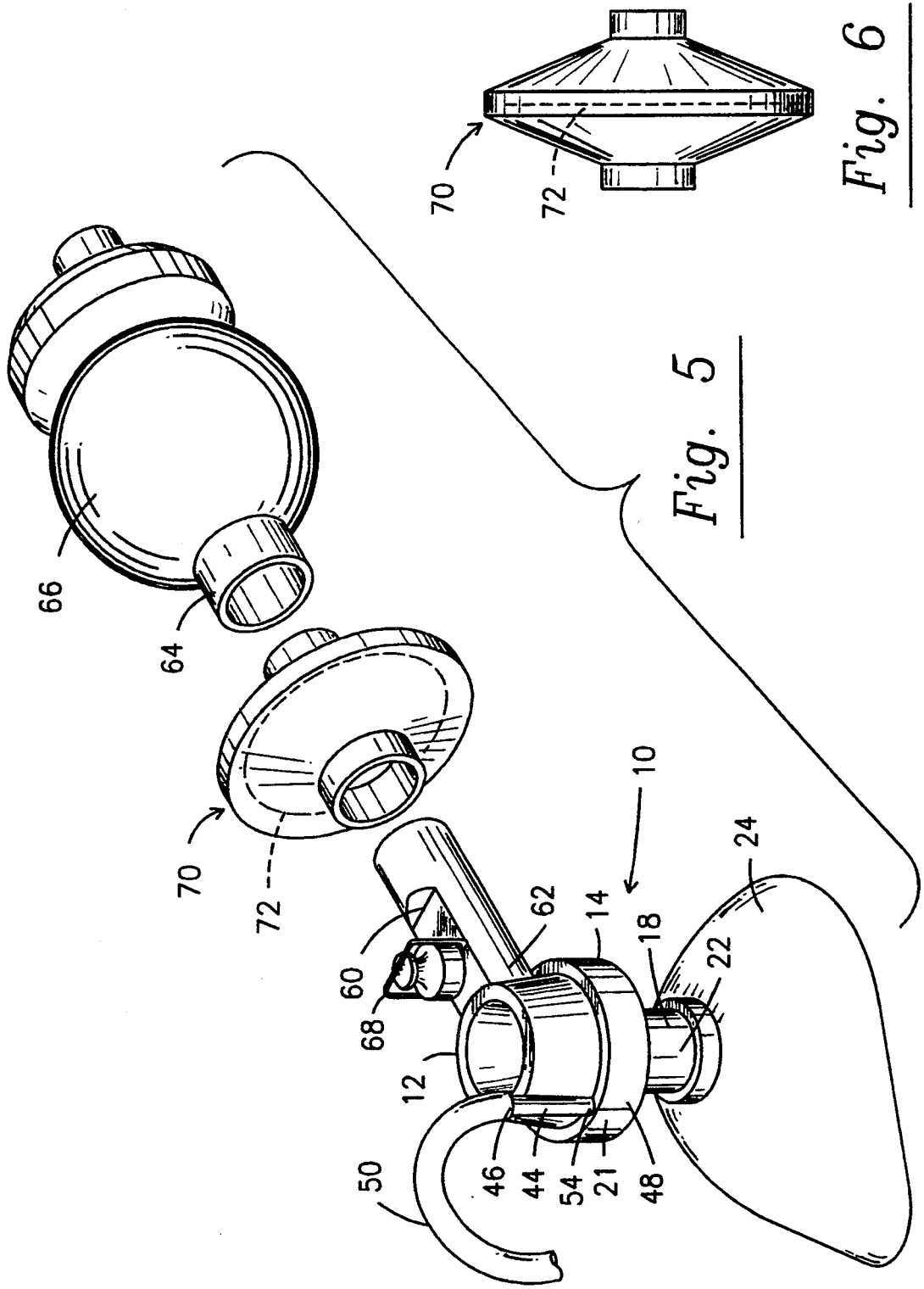

5,357,951

CARDIAC PULMONARY RESUSCITATOR APPARATUS VALVE WITH INTEGRAL AIR SAMPLING PORT

BACKGROUND OF THE INVENTION

1. Field of the Invention

This invention relates to a cardiac pulmonary resuscitator apparatus, More particularly it relates to a cardiac pulmonary resuscitator apparatus having an improved patient valve with an integral air sampling port.

2. Description of Prior Art

Cardiac pulmonary resuscitator apparatus is known and used frequently in emergency medical procedures and in hospital or patient care settings, Medical technicians use the resuscitator apparatus to restore a patient's breathing pattern or to assist a patient who can not breath on their own.

An emergency medical technician squeezes a resuscitator bag attached at a first end to a valve causing air to flow through the valve and into the patient's lungs via a face mask or endotracheal tube attached to the valve, An oxygen reservoir bag may be attached to the resuscitator bag at a second end to administer air flow to the patient, Various air sampling devices are used with the resuscitator apparatus to make readings of the air pressure and carbon dioxide level that is emanating from the air source and patient's lung, The air sampling devices are attached to the resuscitator apparatus intermediate the face mask or endotracheal tube and the valve by way of a connector, This type of external attachment necessitates additional components and expending time for proper connection of those additional components as well as adding dead space in the patient cycle. In many emergency situations the expenditure of time for proper connection of the air sampling device could be critical. There is a need for a cardiac pulmonary resuscitator apparatus with an integral air sampling port in the valve portion of the apparatus for quick and efficient engagement with an air sampling device.

In a hospital or patient care setting patients are often administered air continuously through a ventilator circuit which must be serviced every forty-eight hours. The resuscitator apparatus is used to assist a patient's breathing while the ventilator circuit is being serviced. The patient is placed back on the ventilator circuit after it is fully serviced whereby the resuscitator apparatus is disposed of. The disposal of the resuscitator apparatus causes excessive material waste as well as additional cost to the hospital or patient care facility. There is a need for a filtering attachment intermediate the resuscitator bag and patient valve that will prevent contamination of the resuscitator bag and enable the resuscitator bag to be reused thereby limiting hospital material waste and lowering costs.

SUMMARY OF THE INVENTION

I have invented an improved patient valve with an integral air sampling port for use with a cardiac pulmonary resuscitator apparatus which adds no dead space.

The patient valve has a bottom and top portion joined together forming a cylindrical housing. A diaphragm is mounted between the housing top and bottom portions through which air passes to and from the patient. A rigid tubular port integral with the top portion is mounted parallel to the central axis of the top portion. A first end of the tubular port is connected to a flexible tube leading to an air sampling device and a second end leads into the interior of the top portion and has an opening between a pair of stops along an inner wall of the top portion. The diaphragm abuts up to the stops. A small air passage is retained to permit air flow to the sampling device.

An alternate configuration of the cardiac pulmonary resuscitator apparatus with integral air sampling port has a filter having a housing and enclosed filter element, intermediate the patient valve and resuscitator bag. This filter can be used to prevent fluid or bacteria passage into the resuscitator bag.

BRIEF DESCRIPTION OF THE DRAWINGS

The invention may be best understood by those having ordinary skill in the art by reference to the following detailed description when considered in conjunction with the accompanying drawings in which:

FIG. 4 is a bottom plan view of the top portion of the patient valve;

FIG. 5 is an exploded view of an alternate configuration of the cardiac pulmonary resuscitator apparatus showing the patient valve, filter, and resuscitator bag;

FIG. 6 is a side view of the filter housing with a filter element in phantom;

DETAILED DESCRIPTION OF THE INVENTION

Figure 1:
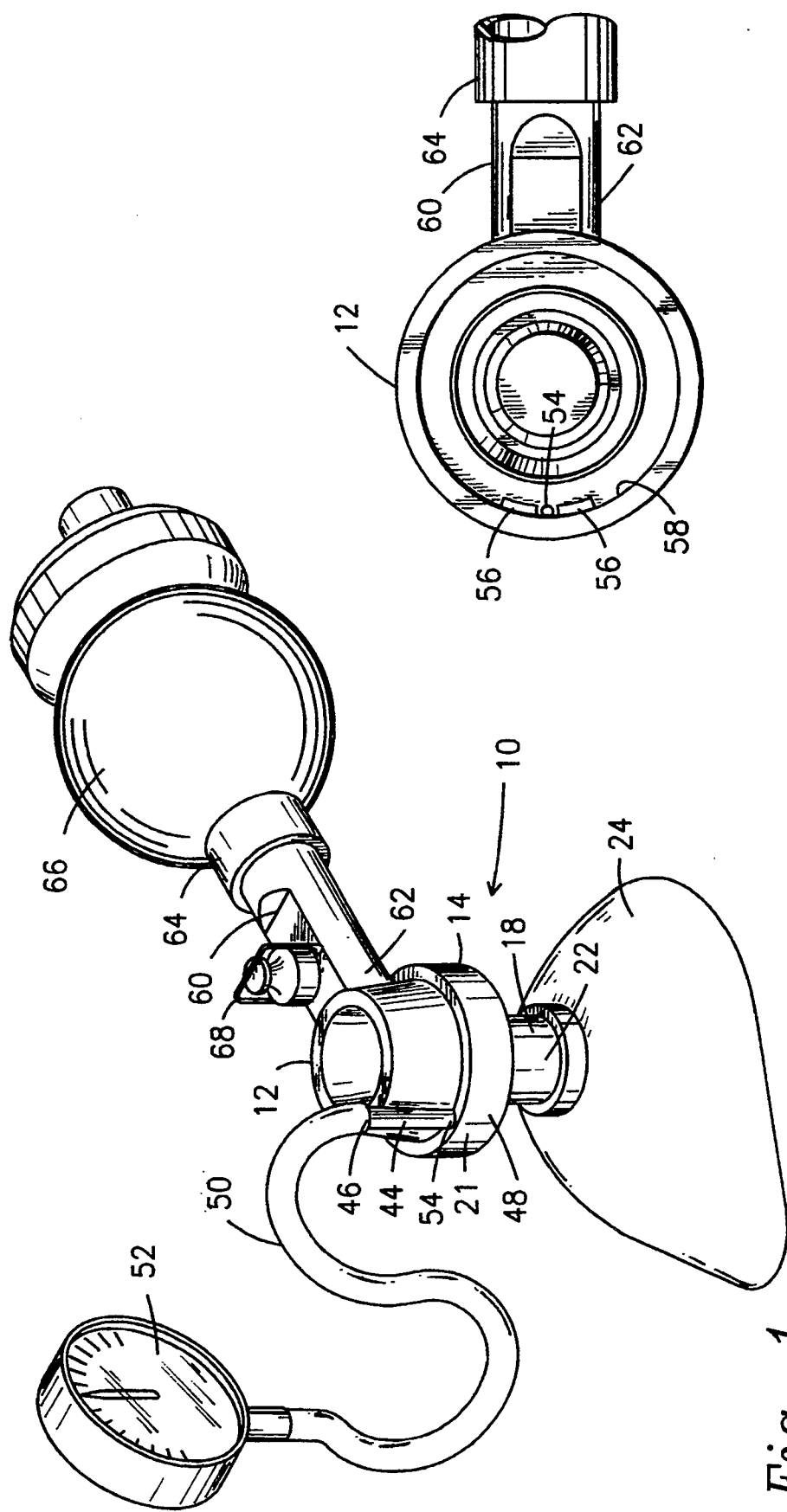
FIG. 1 is a perspective view of the cardiac pulmonary resuscitator apparatus.

Throughout the following detailed description, the same reference numerals refer to the same elements in all figures.

Figure 2:
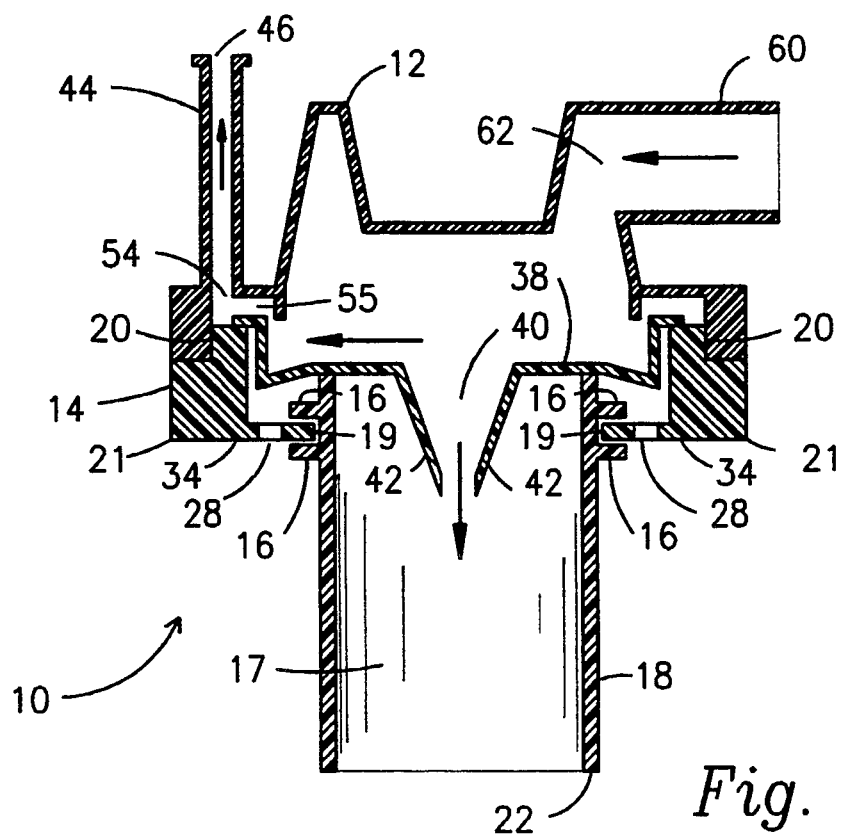
FIG. 2 is a side view in section of the patient valve with the air flow generated from a resuscitator bag.
Figure 3:
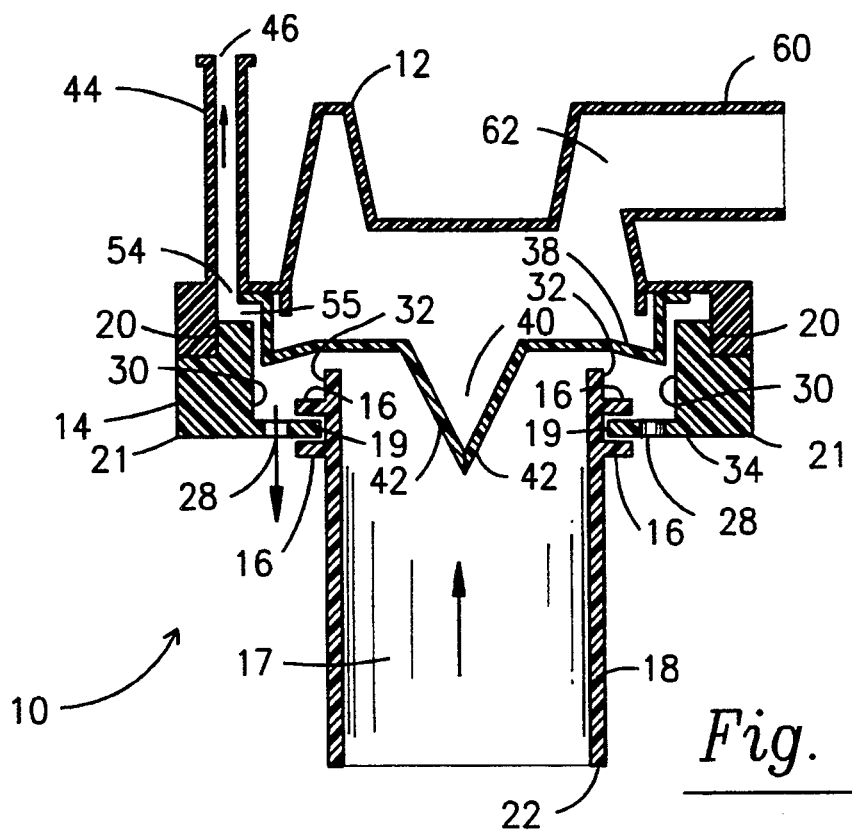
FIG. 3 is a side view in section of the patient valve with the air flow generated from a patient.
Figure 7:
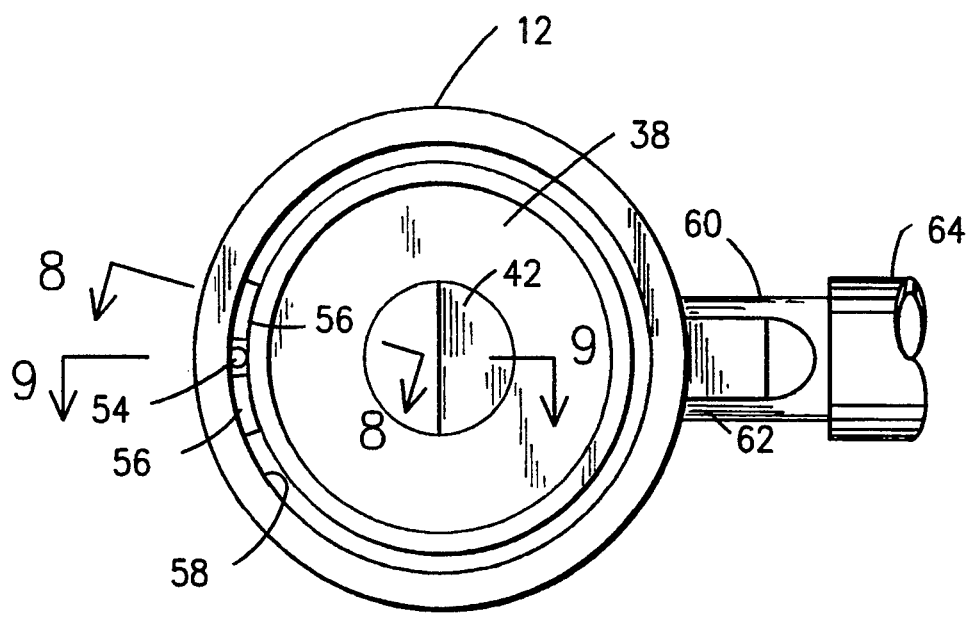
FIG. 7 is a bottom plan view of the top portion of the patient valve with the diaphragm in position.
Figure 8:
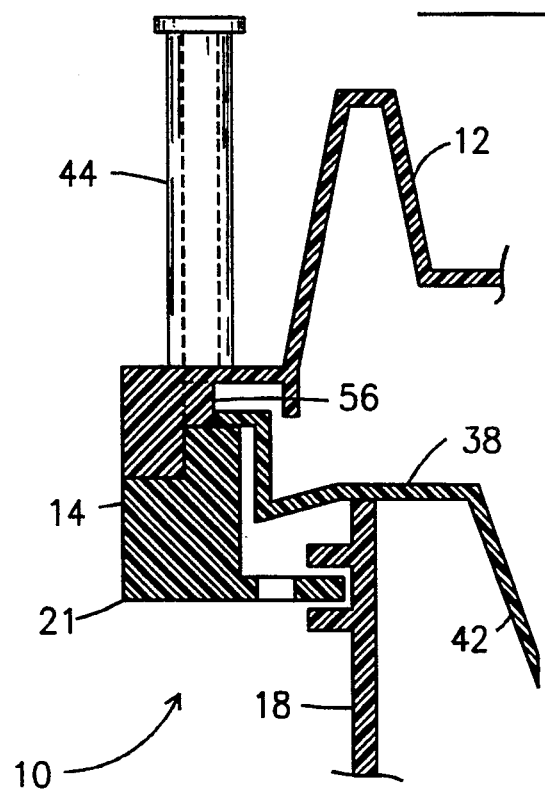
FIG. 8 is a sectional elevational view through line 8—8 of FIG. 7.
Figure 9:
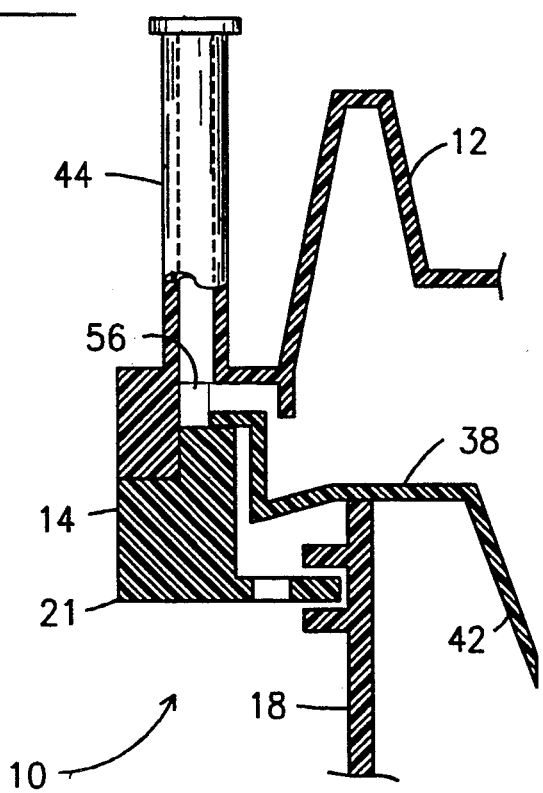
FIG. 9 is a sectional elevational view through line 9—9 of FIG. 7.

In the patient valve, shown in FIG. 1, a cylindrical patient valve housing 10 has a top and bottom portion 12 and 14 respectively. The bottom portion 14 has a central bore 17 inside a rotatable tubular member 18 as shown in FIGS. 2 and 3. The rotatable tubular member 18 has a pair of flanges 16 on each side of a shelf 19 of an annular diaphragm support element 21 integral with bottom portion 14 as shown in FIGS. 2 and 3. This configuration allows tubular member 18 to rotate. The bottom portion 14 is attached by gluing or ultrasonic weld at a first end 20 to the top portion 12 of the cylindrical patient valve housing 10. A distal end 22 of the rotatable tubular member 18 as related to the diaphragm support element 21 attaches to a face mask 24 for use on a patient.

A plurality of air vents 28 are located on a bottom surface 34 of the diaphragm support element 21 between an outer wall 30 and an inner wall 32 integral with the rotatable tubular member 18 as shown in FIGS. 2 and 3. The air vents 28 are covered by a diaphragm 38.

The diaphragm 38 is mounted between the top and bottom portions 12 and 14 respectively of the cylindrical patient valve housing 10. A depression 40, in the diaphragm 38, leads to a pair of valve lips 42, axially extending into the rotatable tubular member 18 as shown in FIGS. 2 and 3. The diaphragm moves between two positions, a first position shown in FIG. 2, providing gaseous communication between the resuscitator bag and the patient's lungs, and a second position shown in FIG. 3, providing gaseous communication between the air vents 28 and the patient's lungs.

A tubular port 44 as shown in FIGS. 1, 2, and 3 is integral with the top portion 12 and is mounted parallel to the central axis of the top portion 12 of the cylindrical patient valve housing 10. The tubular port 44 is attached at a first open end 46 to a hose 50 leading to an air sampling device 52 as shown in FIG. 1. A second open end 54 leads to a space 55 between the top portion 12 and the bottom portion 14 of the cylindrical patient valve housing 10. A pair of stops 56 are juxtaposed to the second open end 54 of the tubular port 44 and are integral with an inner wall 58 of the top portion 12 of the cylindrical patient valve housing 10 as shown in FIG. 4. As shown in FIGS. 2–4, the pair of stops 56 are adjacent to the outer edge of the diaphragm, and prevent the diaphragm from covering the open second end of the tubular port. The tubular port is also positioned adjacent the outer edge of the diaphragm, and is positioned to receive air from both the resuscitator bag and the patient's lungs. In other words, the tubular port acts as a sampling port for gas delivered to the patient, and for gas exhaled by the patient, dependent upon movement of the diaphragm from its first position to its second position, respectively.

A cylindrical tube 60, perpendicular to the central axis of the cylindrical patient valve housing 10, is attached at a first end 62 to the top portion 12 of the cylindrical patient valve housing 10 and at a second end 64 to a cardiac pulmonary resuscitator bag 66 as shown in FIG. 1. A pressure limiting device 68 is mounted on the cylindrical tube 60. The pressure limiting device 68 is fully described in U.S. Pat. No. 4,257,453 and such patent's disclosure is herein incorporated by reference.

An alternate configuration of the cardiac pulmonary resuscitator apparatus has a filter housing 70 intermediate the cylindrical tube 60 of the cylindrical patient valve housing 10 and the resuscitator bag 66 as shown in FIG. 5. A filter element 72 is enclosed inside the filter housing 70, as shown in FIG. 5.

The top and bottom portions 12 and 14 of the cylindrical patient valve housing are sealed together air tight with adhesive or ultrasonic weld and an outer wall of the top and bottom portions 12 and 14 form an outer ring 48 of the cylindrical patient valve housing 10. The diaphragm 38 is inserted inside the cylindrical patient valve housing 10 before the top and bottom portions 12 and 14 are sealed.

The cylindrical patient valve housing 10, rotatable tubular member 18, tubular port 44, cylindrical tube 60, and filter housing 70 are all constructed of a translucent rigid polymer. The diaphragm 38 is constructed of a soft and flexible polymer.

Equivalent mechanical devices can be substituted for the ones set forth above to achieve the same results in the same manner.

Having thus described the invention what is claimed and desired to be secured by Letters Patent is:

1. An improved resuscitator apparatus having a pulmonary resuscitator bag and patient face mask or endotracheal tube joined by a patient valve connected to an air sampling device, the patient valve having a cylindrical housing with a top and bottom portion attached together, a rotatable tubular member connected to the cylindrical patient valve housing and axially extending from the bottom portion of the cylindrical patient valve housing for attachment to the patient face mask or endotracheal tube, a plurality of air vents located on the bottom portion of the cylindrical patient valve housing between an outer wall and inner wall, a diaphragm mounted between the cylindrical patient valve housing top and bottom portions having a depression axially extending into the rotatable tubular member and assembled to permit air flow through a pair of valve lips into the patient face mask or endotracheal tube, a cylindrical tube extending perpendicular with respect to the central axis of the top portion and attached at a first end to the top portion of the cylindrical patient valve housing and at a second end to the cardiac pulmonary resuscitator bag, said diaphragm moving between two positions, a first position providing gaseous communication between said resuscitator bag and the patient's lungs, and a second position providing gaseous communication between the air vents and the patient's lungs, the improvement comprising, means for permitting sampling of gas delivered to the patient, and for sampling gas exhaled by the patient, said sampling means comprising a single tubular port, the tubular port integral with the top portion of said value housing, and mounted on an outer side wall of the top portion parallel to a central axis of the top portion, the tubular port attached at an open first end to a tube leading to an air sampling device and at a second end opening into an interior of the top portion adjacent an outer edge of the diaphragm, said tubular port in gaseous communication with said resuscitator bag when said diaphragm is in said first position, and in gaseous communication with the patient's lungs when said diaphragm is in said second position, and a pair of stops located along an inner wall of the top portion of the cylindrical patient valve housing juxtaposed to the open second end of the tubular port and adjacent to the outer edge of the diaphragm, said pair of stops preventing the diaphragm from covering the open second end of the tubular port.

2. The resuscitator apparatus according to claim 1 wherein the top and bottom portions of the cylindrical patient valve housing are attached together by an adhesive to form a sealed housing.

3. The resuscitator apparatus according to claim 1 wherein the top and bottom portions of the cylindrical patient valve housing are attached together by an ultrasonic weld to form a sealed housing.

4. The resuscitator apparatus according to claim 1 wherein the pair of stops within the cylindrical patient valve housing is a pair of protrusions having a depth about the same as the diameter of the open second end of the tubular port.

5. The resuscitator apparatus according to claim 1 wherein the cylindrical patient valve housing is made from a translucent rigid polymer.

6. The resuscitator apparatus according to claim 1 wherein a filter housing having a filter element is intermediate the patient valve and the pulmonary resuscitator bag.

7. The resuscitator apparatus according to claim 1 wherein the air sampling device is a manometer.

8. The resuscitator apparatus according to claim 1 wherein the air sampling device samples carbon dioxide levels emanating from a patient's lungs.

9. In a patient valve for use in cardiac pulmonary resuscitator apparatus, the patient valve having
    a cylindrical housing having a top and bottom portion,
    a rotatable tubular member integral with the bottom portion of the cylindrical housing and axially extending from the bottom portion, the rotatable tubular member having a central bore,
    a plurality of air vents located on a bottom surface of the bottom portion between an outer and inner wall of the bottom portion,
    a diaphragm mounted between the top portion and bottom portion of the cylindrical housing, the diaphragm having a depression leading to a pair of valve lips leading into the rotatable tubular member central bore, said diaphragm moving between two positions, a first position providing gaseous communication between a gas source and the patient's lungs, and a second position providing gaseous communication between the air vents and the patient's lungs,
    the improvement comprising means for permitting sampling of gas delivered to the patient, and for sampling gas exhaled by the patient, said sampling means comprising a single tubular port, the tubular port integral with the top portion of said value housing, and mounted on an outer side wall of the top portion parallel to a central axis of the top portion, the tubular port attached at an open first end to a tube leading to an air sampling device and at a second end opening into an interior of the top portion adjacent an outer edge of the diaphragm, said tubular port in gaseous communication with said gas source when said diaphragm is in said first position, and in gaseous communication with the patient's lungs when said diaphragm is in said second position, and
    a pair of stops juxtaposed to the open second end of the tubular port and adjacent to the outer edge of the diaphragm, said pair of stops preventing the diaphragm from covering the open second end of the tubular port.

10. A patient valve with integral air sampling port according to claim 9 wherein the diaphragm abuts the pair of stops and permits air flow to the sampling device.

11. A patient valve with integral air sampling port according to claim 10 wherein the pair of stops is a pair of protrusions integral with an inner wall of the top portion, the protrusions having a depth about the same as the diameter of the open second end of the tubular port.

12. A patient valve with integral air sampling port according to claim 9 wherein the cylindrical housing is made from a translucent rigid polymer.

13. A patient valve with integral air sampling port according to claim 9 wherein the are pair of stops integral with an inner wall of the top portion of the cylindrical housing.

14. A patient valve with integral air sampling port according to claim 9 wherein the top and bottom portions of the cylindrical housing are sealed together by an adhesive.

15. A patient valve with integral air sampling port according to claim 9 wherein the top and bottom portions of the cylindrical housing are sealed together by an ultrasonic weld.

16. A patient valve for use in a cardiac pulmonary resuscitator apparatus, the patient valve comprising,
    a diaphragm for controlling air flow mounted between a top and bottom portion of a valve housing, said diaphragm moving between two positions, a first position providing gaseous communication between a gas source and the patient's lungs, and a second position providing gaseous communication between an exhalation flow path and the patient's lungs,
    means for permitting sampling of gas delivered to the patient, and for sampling gas exhaled by the patient, said sampling means comprising a single tubular port mounted on an outer wall of the valve housing,
    a first end of the tubular port connected to a flexible tube leading to an air sampling device and a second end opening leading into the interior of the valve housing adjacent an outer edge of the diaphragm, said tubular port in gaseous communication with said gas source when said diaphragm is in said first position, and in gaseous communication with the patient's lungs when said diaphragm is in said second position, and
    a pair of stops mounted on an inner wall of the valve housing and adjacent to the outer edge of the diaphragm, said pair of stops preventing the diaphragm from covering the second end opening of the tubular port so that air flowing from the patient and the gas source may flow freely through the second end opening to the air sampling device.

* * * * *